United States Patent
Kang et al.

(10) Patent No.: US 9,870,960 B2
(45) Date of Patent: Jan. 16, 2018

(54) CAPACITANCE MONITORING USING X-RAY DIFFRACTION

(71) Applicant: International Business Machines Corporation, Armonk, NY (US)

(72) Inventors: Donghun Kang, Hopewell Junction, NY (US); Kriteshwar K. Kohli, Fishkill, NY (US); Oh-jung Kwon, Hopewell Junction, NY (US); Anita Madan, Danbury, CT (US); Conal E. Murray, Yorktown Heights, NY (US)

(73) Assignee: International Business Machines Corporation, Armonk, NY (US)

( * ) Notice: Subject to any disclaimer, the term of this patent is extended or adjusted under 35 U.S.C. 154(b) by 391 days.

(21) Appl. No.: 14/575,134

(22) Filed: Dec. 18, 2014

(65) Prior Publication Data

US 2016/0178679 A1    Jun. 23, 2016

(51) Int. Cl.
*H01L 21/00* (2006.01)
*H01L 21/66* (2006.01)
*G01N 23/20* (2006.01)
*G01R 31/265* (2006.01)

(52) U.S. Cl.
CPC .............. *H01L 22/14* (2013.01); *G01N 23/20* (2013.01); *G01R 31/2656* (2013.01); *H01L 22/12* (2013.01)

(58) Field of Classification Search
CPC .... G01N 23/20; G01R 31/2656; H01L 22/14; H01L 22/12
See application file for complete search history.

(56) References Cited

U.S. PATENT DOCUMENTS

| 6,156,623 | A  | 12/2000 | Hendrix et al. |
| 6,180,252 | B1 | 1/2001  | Farrell et al. |
| 6,235,572 | B1 | 5/2001  | Kunitomo et al. |
| 6,445,025 | B2 | 9/2002  | Suenaga et al. |
| 6,541,331 | B2 | 4/2003  | Chudzik et al. |
| 6,569,249 | B1 | 5/2003  | Singh et al. |
| 6,874,369 | B2 | 4/2005  | Yokoyama et al. |

(Continued)

FOREIGN PATENT DOCUMENTS

| CN | 102786093 A  | 11/2012 |
| CN | 102320826 B  | 7/2013  |
| WO | 2012062540 A1 | 5/2012 |

OTHER PUBLICATIONS

Ertas et al., "X-ray photoelectron spectroscopy for resistance-capacitance measurements of surface structures", Applied Physics Letters, vol. 86, 183110, (2005), pp. 183110-1-183110-3.

(Continued)

*Primary Examiner* — Richard Booth
(74) *Attorney, Agent, or Firm* — L. Jeffrey Kelly

(57) ABSTRACT

A method includes measuring a difference between a primary X-ray diffraction peak and a secondary X-ray diffraction peak, the primary X-ray diffraction peak corresponds to an unstrained portion of a semiconductor substrate and the secondary X-ray diffraction peak corresponds to a strained portion of the semiconductor substrate, the difference between the primary X-ray diffraction peak and the secondary X-ray diffraction peak includes a delta shift peak that corresponds to changes in a crystal lattice caused by a stress applied to the strained portion of the semiconductor substrate, the delta shift peak includes variations in a deep trench capacitance.

20 Claims, 8 Drawing Sheets

(56) References Cited

U.S. PATENT DOCUMENTS

| | | |
|---|---|---|
| 6,900,498 B2 | 5/2005 | Stauf et al. |
| 7,378,719 B2 | 5/2008 | Yang |
| 7,433,051 B2 | 10/2008 | Owen |
| 8,524,632 B2 | 9/2013 | Gadkaree et al. |
| 2012/0113561 A1 | 5/2012 | Chin |
| 2013/0121470 A1 | 5/2013 | Toraya et al. |

OTHER PUBLICATIONS

Wonsiewicz et al., "Electrical properties of metal-SiO2-silicon structures under mechanical stress", J. Appl. Phys., vol. 44, No. 12, Dec. 1973, pp. 5476-5479.

CAPACITANCE MONITORING USING X-RAY DIFFRACTION

BACKGROUND

The present invention generally relates to semiconductor devices and more particularly to monitoring capacitance changes in deep trench (DT) capacitors using X-ray diffraction (XRD) measurements.

Deep trenches may be used in the semiconductor industry to provide a variety of useful devices including deep trench (DT) capacitors. The deep trenches may be formed in the semiconductor substrate and may typically include a depth exceeding 1 micrometer, or 1 micron, in contrast to shallow trenches having a depth less than 1 micron. The deep trenches may be generally utilized in a stand-alone semiconductor circuit such as a dynamic random access memory (DRAM) circuit to provide DT capacitors.

Typically, DT capacitors are formed in the semiconductor substrate (e.g. silicon wafer) using one or more conventional techniques, such as reactive ion etching (RIE), with photoresist or other materials as a mask to cover the areas where trench formation may not be desired. The deep trench may be typically filled with a conductor material (most commonly n-type doped polysilicon), which may serve as one plate of the capacitor, usually referred to as the "storage node." The second plate of the capacitor may be typically formed by out diffusion of an n-type doped region surrounding the lower portion of the trench, usually referred to as the "buried plate." A node dielectric layer, which may include, for example, silicon dioxide ($SiO_2$), silicon nitride (SiN), silicon oxynitride (SiON), tantalum oxide ($Ta_2O_5$), aluminum oxide ($Al_2O_3$), or any other dielectric material, may be provided to separate the storage node and buried plate, thereby forming the DT capacitor. Field effect transistor (FET) devices may be formed in the semiconductor substrate adjacent to the DT capacitors. The capacitance value of the deep trench may depend on the size of the deep trench area. Typically, the deeper the deep trench, the larger the capacitance value.

Deep trench parameters such as volume and surface area may have significant impact on the DT capacitor characteristics including capacitance, resistance, and leakage current. Typical approaches for assessing DT trench capacitors may include destructive and nondestructive electrical testing. The capacitance of the deep trench may be one of the most important parameters for trench DRAM, embedded DRAM, application specific integrated circuits (ASICs), and system-on-chip products. By knowing the deep trench capacitance, evaluation of process integrity and prediction of device parameters may be conducted for process optimization. However, in current semiconductor fabrication technology, deep trench capacitance may be directly measured only after wafers reach the end of the process.

SUMMARY

According to an embodiment of the present disclosure a method may include measuring a difference between a primary X-ray diffraction peak and a secondary X-ray diffraction peak, the primary X-ray diffraction peak may correspond to an unstrained portion of a semiconductor substrate and the secondary X-ray diffraction peak may correspond to a strained portion of the semiconductor substrate, the difference between the primary X-ray diffraction peak and the secondary X-ray diffraction peak may include a delta shift peak corresponding to changes in a crystal lattice caused by a stress applied to the strained portion of the semiconductor substrate, the delta shift peak may include variations in a deep trench capacitance.

According to another embodiment of the present disclosure, a method may include forming a deep trench on a substrate, conducting a first X-ray diffraction measurement on the substrate, a first X-ray diffraction peak may be observed in the first X-ray diffraction measurement, depositing a high-k dielectric material on the substrate and in the deep trench, conducting a second X-ray diffraction measurement on the substrate, a second X-ray diffraction peak is observed in the second X-ray diffraction measurement, measuring a difference between a center of the first X-ray diffraction peak and a center of the second X-ray diffraction peak, the difference between the center of the first X-ray diffraction peak and the center of the second X-ray diffraction peak may include a delta peak shift, correlating, using a database, a plurality of previously measured delta peak shift and deep trench capacitance values to obtain a correlation curve, a lower capacitance limit and an upper capacitance limit may be set in the correlation curve based on the database, and comparing to the correlation curve the delta peak shift to determine a deep trench capacitance value, where continuing processing of the substrate may depend on the deep trench capacitance value being above the lower capacitance limit and below the upper capacitance limit set in the correlation curve.

According to another embodiment of the present disclosure, a computer program product may include a computer readable non-transitory article of manufacture tangibly embodying computer readable instructions which, when executed, cause a computer to carry out a method comprising conducting a first X-ray diffraction measurement on a substrate before forming a deep trench in the substrate, a first X-ray diffraction peak may be observed in the first X-ray diffraction measurement, conducting a second X-ray diffraction measurement on the substrate after depositing a high-k dielectric material in the deep trench, a second X-ray diffraction peak may be observed in the second X-ray diffraction measurement, measuring a difference between a center of the first X-ray diffraction peak and a center of the second X-ray diffraction peak, the difference between the center of the first X-ray diffraction peak and the center of the second X-ray diffraction peak may include a delta peak shift, correlating, using a database, a plurality of previously measured delta peak shift and deep trench capacitance values to obtain a correlation curve, a lower capacitance limit and an upper capacitance limit may be set in the correlation curve based on the database, and comparing to the correlation curve the delta peak shift to determine a deep trench capacitance value, where continuing processing of the substrate may depend on the deep trench capacitance value being above the lower capacitance limit and below the upper capacitance limit set in the correlation curve.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
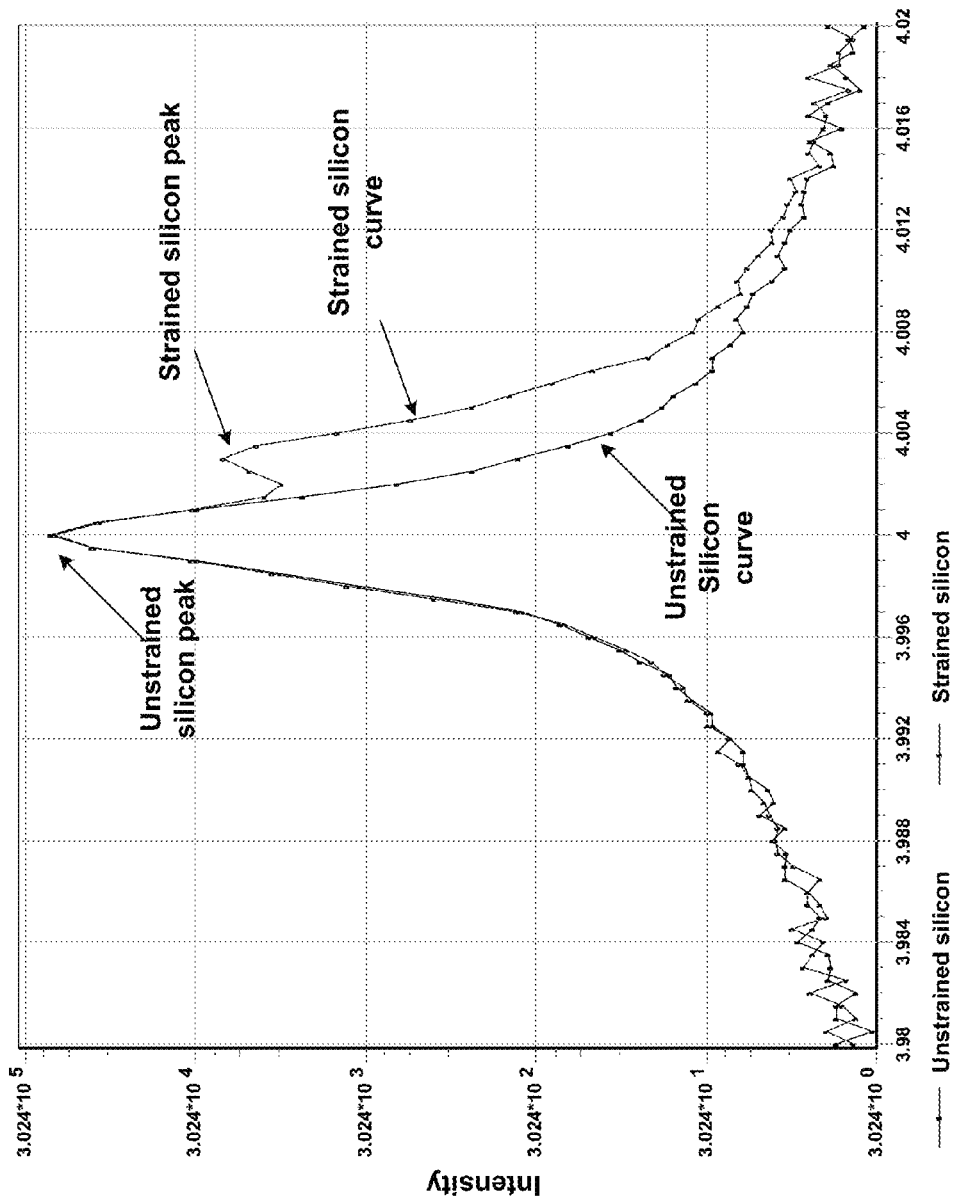
FIG. 1 is a plot depicting exemplary results from X-ray diffraction measurements, according to an embodiment of the present disclosure.

Exemplary embodiments now will be described more fully herein with reference to the accompanying drawings, in which exemplary embodiments are shown. This disclosure may, however, be embodied in many different forms and should not be construed as limited to the exemplary embodiments set forth herein. Rather, these exemplary embodiments are provided so that this disclosure will be thorough and complete and will fully convey the scope of this disclosure to those skilled in the art. In the description, details of well-known features and techniques may be omitted to avoid unnecessarily obscuring the presented embodiments.

For purposes of the description hereinafter, terms such as "upper", "lower", "right", "left", "vertical", "horizontal", "top", "bottom", and derivatives thereof shall relate to the disclosed structures and methods, as oriented in the drawing figures. Terms such as "above", "overlying", "atop", "on top", "positioned on" or "positioned atop" mean that a first element, such as a first structure, is present on a second element, such as a second structure, wherein intervening elements, such as an interface structure may be present between the first element and the second element. The term "direct contact" means that a first element, such as a first structure, and a second element, such as a second structure, are connected without any intermediary conducting, insulating or semiconductor layers at the interface of the two elements.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is rather focused on the distinctive features or elements of various embodiments of the present invention.

The following described exemplary embodiments provide a system, method and program product for monitoring capacitance changes in deep trench (DT) capacitors using X-ray diffraction (XRD) measurements.

Several materials and processes used during the fabrication of deep trench (DT) capacitors may distort the crystal lattice of the substrate in which they are formed. Variations in the crystalline structure of the substrate may include deformation and/or dislocations in the crystal lattice of the substrate material, which may be the result of stress applied during fabrication of the DT capacitors. Variations in the crystalline structure of the substrate may alter the actual capacitance value of a DT capacitor depending on the amount of material existing within the capacitor and the stress it applies to the substrate. Since electrical testing for measuring deep trench capacitance is typically performed later in the manufacturing process, numerous processing steps may take place before reaching a point during the process at which electrical testing of the DT capacitor may be conducted. This may cause defects and problems related to device yield to remain unnoticed until the end of the manufacturing process thereby increasing manufacturing time and costs.

Owing to the sensitivity of X-ray diffraction (XRD) measurements to changes in lattice spacing within crystalline materials forming the substrate, deformations and/or dislocations caused by the applied stress in the substrate lattice (e.g. a silicon substrate or silicon wafer lattice structure) may be easily detected by XRD scanning of the substrate. Additionally, XRD equipment is readily available in the fabrication line making scanning of the substrate, and hence DT capacitance estimation, possible at any time during the manufacturing process.

Therefore, by conducting X-ray diffraction measurements, embodiments of the present disclosure may, among other potential benefits, allow in-line scans of the substrate at early steps during the fabrication process, substantially before electrical testing may be performed, to estimate deep trench capacitance variations. As a result, prompt location of damaged regions within the substrate, which may affect functioning of DT capacitors and hence FETs yield and reliability, may be performed.

The present invention generally relates to semiconductor devices and more particularly to monitoring capacitance changes in deep trench (DT) capacitors using X-ray diffraction (XRD) measurements. One way to use XRD for monitoring capacitance changes in DT capacitors may include scanning the substrate before and after a deposition process and measuring a delta peak shift in XRD measurements that may be compared with a pre-established correlation between capacitance and XRD delta peak shift values obtained from a database of experimental data. One embodiment by which to perform in-line XRD diffraction measurements to estimate deep trench capacitance is described in detail below by referring to the accompanying drawings in FIGS. 1-5.

Referring now to FIG. 1, a plot showing exemplary results from X-ray diffraction (XRD) measurements on a substrate is depicted, according to an embodiment of the present disclosure. The substrate may include, for example, a silicon substrate or silicon wafer. However, the substrate may include any other semiconductor material known in the art.

In this exemplary embodiment, the XRD scan results may include an unstrained silicon curve and a strained silicon curve. The unstrained silicon curve may contain information related to the behavior of an area of the substrate under normal conditions (no stress applied). The unstrained silicon curve may include a diffraction peak at the center of the unstrained silicon curve (unstrained silicon peak), this peak may correspond to a lattice spacing in areas of the substrate without deep trench capacitors.

Simultaneously, the strained silicon curve is displayed in the XRD scan results illustrated in the figure. The strained silicon curve may include information of the substrate material when a stress is applied. For example, the strained silicon curve may include information of an area of the silicon substrate where deep trench capacitors are formed. At this point, the unstrained silicon curve may serve as a reference for comparison and analysis purposes.

As illustrated in the figure, the strained silicon curve may exhibit an additional diffraction peak (strained silicon peak). This additional or secondary diffraction peak in the strained silicon curve may be the result of deformations in the crystal lattice of the silicon substrate caused by the deep trench capacitors. Consequently, by comparing the unstrained silicon curve and the strained silicon curve, the impact of deep trench capacitors in the silicon substrate may be assessed. It should be noted that this analysis may be performed in precise locations of the substrate, specifically where deep trenches are formed at any time during the manufacturing process.

Figure 2:
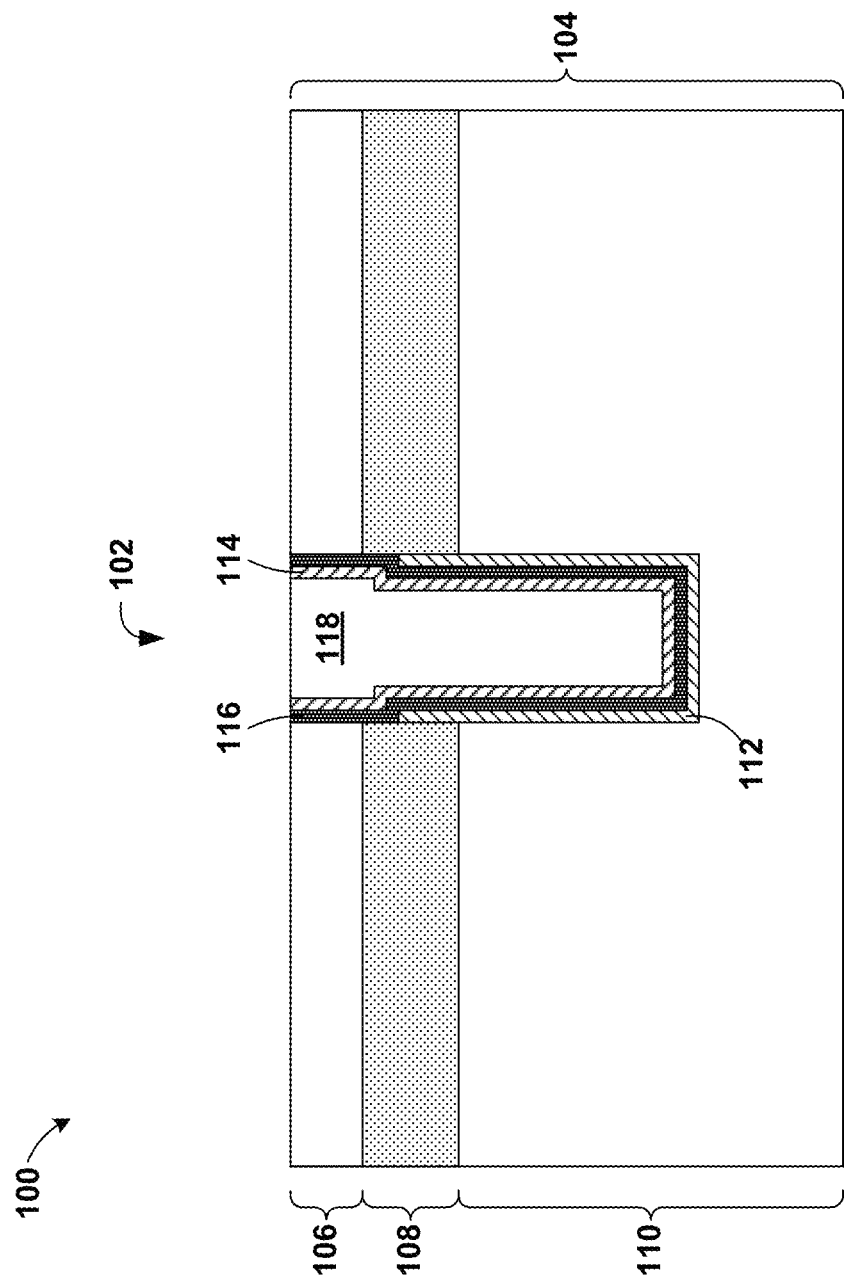
FIG. 2 is a cross-sectional view of a semiconductor structure depicting forming a deep trench on a substrate, according to an embodiment of the present disclosure.

Referring now to FIG. 2, a deep trench capacitor 102 is fabricated in a substrate 104 of a semiconductor structure 100 in accordance with an exemplary embodiment. The substrate 104 may include any semiconductor material including, but not limited to: Si, SiC, SiGe, SiGeC, Ge alloys, GaAs, InAs, InP, as well as other III-V or II-VI compound semiconductors. The substrate 104 may also be comprised of a layered semiconductor structure such as Si/SiGe, a silicon-on-insulator structure or a SiGe-on-insulator structure. In some embodiments of the present invention, it is preferred that the substrate 104 be composed of a silicon-containing semiconductor material, for example a semiconductor material that includes silicon. The substrate 104 may be doped, undoped or contain doped and undoped regions therein (not shown). The doped device regions are typically known or referred to as "wells".

In the specific embodiment shown in FIG. 2, the deep trench capacitor 102 may be formed in a semiconductor-on-insulator (SOI) substrate 104 that contains a semiconductor layer 106, a buried insulator layer 108, and a semiconductor base layer 110 (hereinafter "base layer") that is located underneath the buried insulator layer 108. The semiconductor layer 106 may include any of the several semiconductor materials included in the base layer 110. In general, the base layer 110 and the semiconductor layer 106 may include either identical or different semiconducting materials with respect to chemical composition, dopant concentration, and crystallographic orientation. In one embodiment of the present invention, the base layer 110 and the semiconductor layer 106 may include semiconducting materials that include at least different crystallographic orientations. Typically the base layer 110 or the semiconductor layer 106 include a {110} crystallographic orientation and the other of the base layer 110 or the semiconductor layer 106 includes a {100} crystallographic orientation. Typically, the semiconductor layer 106 includes a thickness ranging from about 5 nm to about 100 nm. Methods for making the semiconductor layer 106 are well known in the art. Non-limiting examples include SIMOX (Separation by Implantation of Oxygen), wafer bonding, and ELTRAN® (Epitaxial Layer TRANsfer).

The buried insulator layer 108 may be formed from any of several dielectric materials known in the art. Non-limiting examples include, for example, oxides, nitrides, and oxynitrides of silicon. Oxides, nitrides and oxynitrides of other elements are also envisioned. In addition, the buried insulator layer 108 may include crystalline or non-crystalline dielectric material. Moreover, the buried insulator layer 108 may be formed using any of several known methods. Non-limiting examples include ion implantation methods, thermal or plasma oxidation or nitridation methods, chemical vapor deposition methods and physical vapor deposition methods. In one embodiment, the buried insulator layer 108 may be about 150 nm thick. Alternatively, the buried insulator layer 108 may include a thickness ranging from about 10 nm to about 500 nm.

The base layer 110 may be made from any of several known semiconductor materials such as, for example, a bulk silicon substrate. Other non-limiting examples include silicon, germanium, silicon-germanium alloy, silicon carbide, silicon-germanium carbide alloy, and compound semiconductor materials. Non-limiting examples of compound semiconductor materials include gallium arsenide, indium arsenide, and indium phosphide. Typically, the base layer 110 may be about, but is not limited to, several hundred microns thick. For example, the base layer 110 may include a thickness ranging from 0.5 mm to about 1.5 mm. While this embodiment of the invention is illustrated using a SOI substrate, it is understood that the present invention can be easily extended to a bulk semiconductor substrate, and the possible difference in process steps for the SOI substrate and the bulk semiconductor substrate, if any, will be mentioned at the appropriate steps to be described hereinafter.

In an embodiment, the deep trench capacitor 102 may include an outer or bottom electrode 112 and an inner or top electrode 114 separated by an insulating layer or node dielectric 116. In the present example, the inner and outer electrode 112, 114 may consist of thin metallic layers. A polysilicon fill material 118 may be formed directly on top of the inner electrode 114 and substantially fill the deep trench. In other embodiments the outer electrode 112 may consist of a doped portion of the base layer 110 otherwise referred to as a buried plate and the inner electrode may consist of a fill layer, of either metal or doped semiconductor material, which may substantially fill the deep trench capacitor.

The node dielectric layer 116 may include any dielectric material, including, but not limited to: hafnium oxide, barium strontium oxide, etc., and it may be deposited by any suitable dielectric deposition technique, including, but not limited to: chemical vapor deposition (CVD), atomic layer deposition (ALD), or physical vapor deposition (PVD). In an embodiment, the node dielectric layer 116 includes a high-k dielectric material with a dielectric constant of not less than 4.0, which allows formation of a shallower trench at a given capacitance and therefore functions to further reduce the required device processing time and complexity.

It should be noted that the deep trench capacitor 102 of FIG. 2 is only an exemplary configuration and that embodiments of the present disclosure are applicable to any deep trench capacitor configuration having an insulating layer similar to the node dielectric 116.

Figure 3:
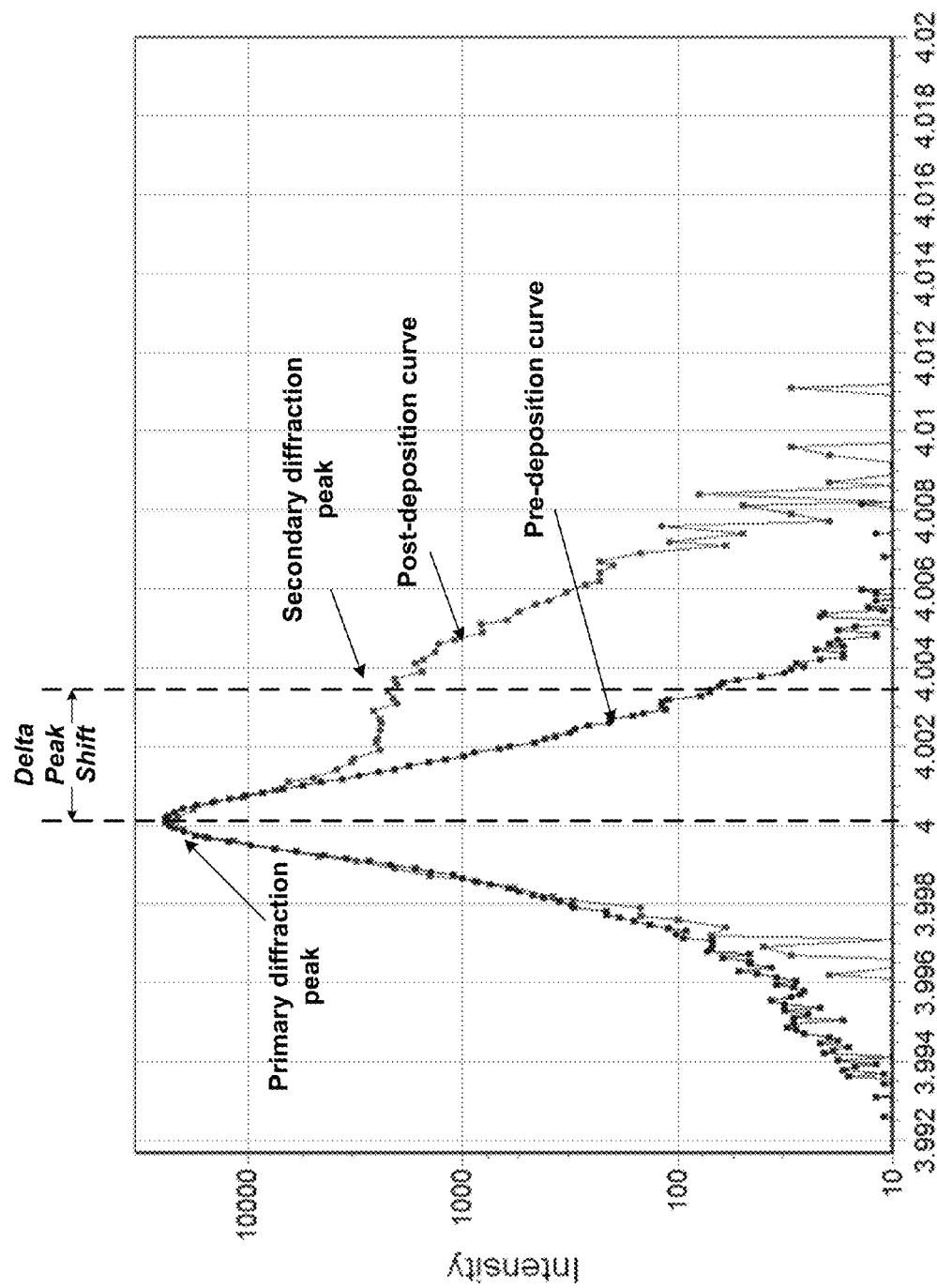
FIG. 3 is a plot depicting results from X-ray diffraction measurements before and after a deposition process, according to an embodiment of the present disclosure.

Referring now to FIG. 3, a plot showing results from XRD measurements on a substrate before and after a deposition process is shown, according to an embodiment of the present disclosure. More specifically, a first curve (pre-deposition curve) may include XRD measurements before depositing a high-k dielectric thin film on the substrate and a deep trench, similar to the node dielectric 116 (FIG. 2). Deposition of high-k dielectric films may be typical during formation of deep trench capacitors in, for example, DRAM manufacturing technology. Deposition of high-k dielectric films is typical and well-known to those skilled in the art and may involve processes such as, for example, CVD, ALD, or PVD, as described above with reference to FIG. 2. A first or primary diffraction peak may be observed in the pre-deposition curve.

A second curve (post-deposition curve) may also be included in the XRD scan results. The post-deposition curve may include XRD measurements of the silicon substrate after the high-k dielectric has been deposited in the deep trenches. As may be observed in the figure, there is a secondary diffraction peak in the post-deposition curve which may indicate the presence of deformations in the substrate caused by the stress applied during the deposition process as described above.

By comparing the pre-deposition curve (reference curve) and the post-deposition curve, a variation between the primary and secondary diffraction peaks, also referred to as a delta peak shift, may be detected and measured as illustrated in the figure. More specifically, the delta peak shift may include a difference between centers of the primary diffraction peak and the secondary diffraction peak. This difference (delta peak shift) may be measured and correlated to changes in the deep trench capacitance as will be described in detail below. It should be noted that any known XRD tool may be used to scan the substrate and calculate the delta peak shift.

Figure 4:
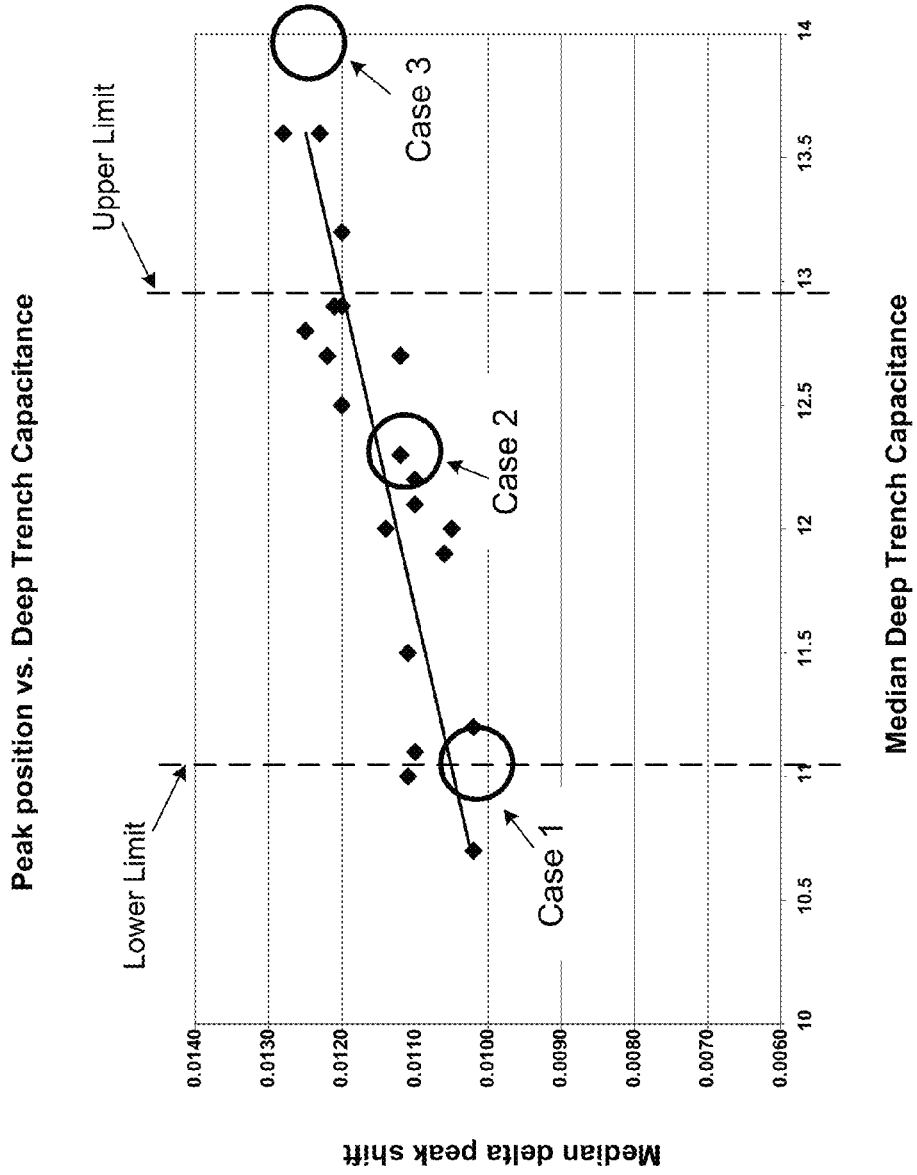
FIG. 4 is a plot depicting a correlation between a shift in position of an X-ray diffraction peak and deep trench capacitance, according to an embodiment of the present disclosure.

Referring now to FIG. 4, a plot depicting a correlation between a shift in the XRD delta peak and deep trench capacitance is shown, according to an embodiment of the present disclosure. The correlation between deep trench capacitance and the shift in peak position (delta peak shift) may be generated by calibration with previously conducted electrical measurements. More specifically, a database of capacitance and XRD delta peak shift values obtained from actual electrical measurements performed on numerous substrates (e.g. wafers) may be used to establish a correlation curve between the delta peak shift and capacitance. Once the correlation between experimental delta peak shift and capacitance values have been established, the measured delta peak shift in the processing substrate (FIG. 3) may be compared with the correlated values as will be described in detail below.

According to an embodiment, the x-axis of the correlation curve may include deep trench capacitance values from the database, these capacitance values are obtained from measurements performed in the deep trench capacitors at those points during the manufacturing process at which electrical testing is typically allowed. The y-axis may include experimental measurements of delta peak shift performed in different regions of a plurality of substrates (e.g. previously processed wafers) containing deep trenches before and after a deposition process. To form the correlation, XRD measurements were performed before and after electrical testing took place in the processing substrate. By doing so, upper and lower bounds and a medium value may be established for capacitance in the deep trenches. More specifically, by establishing upper, lower, and medium capacitance values, the corresponding delta peak shift for a determined capacitance value may be identified. This may allow one to determine if a substrate may yield good capacitance or not, for example, if the measured delta peak shift in an area of a processing substrate is outside of the established capacitance limits then the manufacturing process may be stopped and the substrate may be retired for further analysis saving manufacturing time.

For example, the dotted lines in the figure illustrate a pre-established lower limit and upper limit for deep trench capacitance. The lower and upper capacitance limits may be selected based on records of deep trench capacitance values available in this technology from databases of previous electrical measurements. Then, during processing, the delta peak shift of an area within the processing substrate may be measured as described above with reference to FIG. 3 and compared with the correlated values of delta peak shift and deep trench capacitance shown in the figure.

For example, in Case 1 a processing silicon substrate (such as the one described in FIG. 3) may include an XRD peak shift corresponding to a capacitance value close to the lower limit. In Case 2 the same silicon substrate may have a measured XRD peak shift corresponding to a capacitance value within the pre-established capacitance limits, and in Case 3 it may include a measured XRD peak shift corresponding to a capacitance value substantially outside the specified upper limit. It should be noted that in these exemplary cases, the processing silicon substrate in Case 1 and Case 3 may be scrapped from the manufacturing line before actual electrical testing may be performed, which may in turn reduce manufacturing time.

As described above with reference to FIG. 3, the delta peak shift may correspond to the position of the secondary diffraction peak in the post-deposition curve relative to the unstrained primary diffraction peak in the pre-deposition curve. It should be noted that XRD measurements for detecting the delta peak shift may be conducted in the processing substrate at all stages of the manufacturing process.

The correspondence that exists between the XRD delta peak shift and the deep trench capacitance values may provide a way to pre-screen substrates (e.g. wafers) in-line and at early steps during the fabrication process. It should be noted that this may be possible because the XRD machine is an in-line tool and, as described above, it may allow to project the behavior of the substrate in order to make timely decisions. Additionally, XRD measurements may help locating areas of the substrate in which overlay problems may exist before electrical testing may be conducted in the device.

Figure 5:
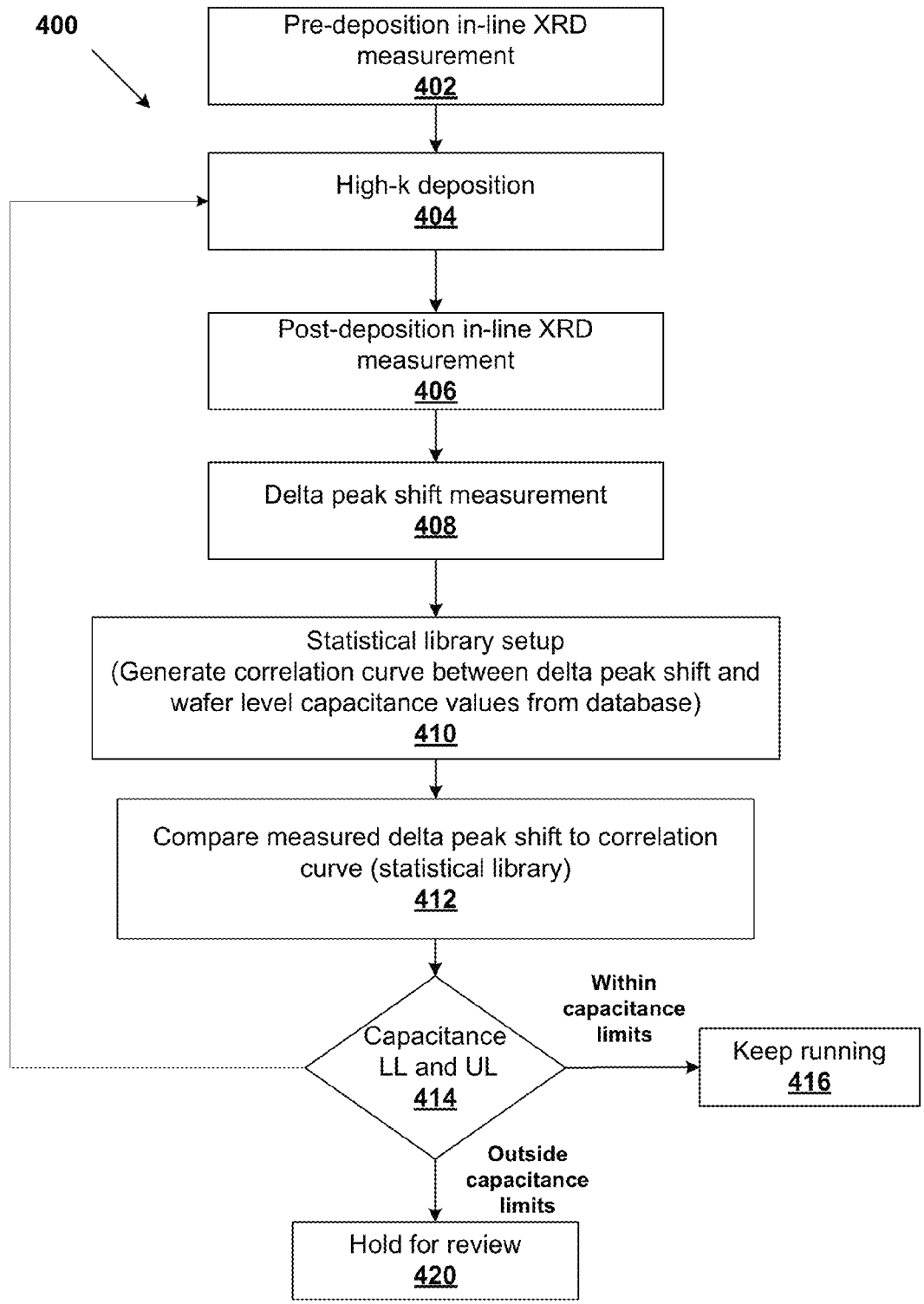
FIG. 5 is a flowchart depicting processing steps of a method to estimate deep trench capacitance based on X-ray diffraction measurements, according to an embodiment of the present disclosure.

Referring now to FIG. 5, a flowchart 400 describing the steps of a method to estimate deep trench capacitance based on XRD measurements is shown, according to an embodiment of the present disclosure. The method may start at step 402 with a first in-line XRD measurement of the substrate prior to deposition of a material of interest. In this embodiment, the material of interest may include a high-k dielectric film. The deposition process may take place at step 404. After the deposition process, a second in-line XRD measurement may be conducted at step 406.

As described above with reference to FIGS. 3 and 4, the difference between the diffraction peaks of the pre-deposition and post-deposition XRD curves may be measured to determine the delta peak shift (step 408). Then a statistical library may be set at step 410 based on experimental results to establish a correlation curve between deep trench capacitance and delta peak shift. The statistical library may include a database of known capacitance and delta peak shift values obtained from previously processed wafers. The correlation curve may include pre-established upper limit (UL) and lower limit (LL) of deep trench capacitance within which may be desired to remain. The delta shift peak measured at step 408 may then be compared at step 412 to the correlation curve of the delta XRD peak shift and deep trench capacitance generated at step 410 which may be substantially similar to the correlation curve depicted in FIG. 4.

At step 414, if the delta peak shift measured at step 408 is outside the pre-established capacitance limits then the substrate may be held for review (step 420) or retired from the manufacturing line. On the other hand, if the delta peak shift measured at step 408 is within the pre-established capacitance limits then the substrate may continue in the manufacturing line (step 416).

For illustration purposes only, without intent of limitation, the steps described above included the deposition of a high-k dielectric material, however the proposed method may be applied to any known material in the art that may induce a stress in the substrate. A correlation between the applied stress and the deformation that may be generated in the substrate may be expressed in terms of the capacitance of the device or any other appropriate metric.

It should be noted that the proposed method may also be used to detect deformation within the semiconductor substrate caused during additional processing steps. More specifically, the proposed method may allow to determine the impact on capacitance or other metrics caused by additional processing steps that may also alter the lattice structure of the semiconductor substrate.

For example, during high temperature annealing substantial amounts of heat may be applied in areas of the substrate which may disrupt its crystal lattice. More specifically, high temperature annealing may cause dislocations in the substrate crystalline structure. Dislocations may be particularly undesired in areas of the substrate in close proximity to active devices, in such an instance the dislocations may act as a short circuit causing the devices to fail. By applying the proposed method, the concentration of dislocations in the substrate may be assessed based on the amount of deformation induced during the high temperature annealing in a non-destructive fashion. The proposed method may provide an estimate of the dislocation density within the semiconductor substrate and its effect on the failure of the devices. A statistical library may include a database of known device leakage values due to dislocations. The measured delta peak shift may then be compared to a correlation curve of the delta XRD peak shift and device leakage which may include a pre-established upper limit of device leakage below which may be desired to remain.

Therefore, by conducting in-line X-ray diffraction measurements a substrate may be scanned at early steps during the fabrication process, substantially before electrical testing may be performed, allowing one to estimate deep trench capacitance variations. As a result defects within the substrate, which may affect deep trench capacitor functioning and hence FETs yield and reliability, may be detected at early stages of the manufacturing process. The steps described in flowchart 400 may provide a substantially sensitive method to detect deformation in a semiconductor substrate and assess their impact on deep trench capacitance values or other metrics, this may be used for process control since defects in the substrate may be detected substantially before it is allowed using traditional electrical testing.

Embodiments of the present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Figure 6:
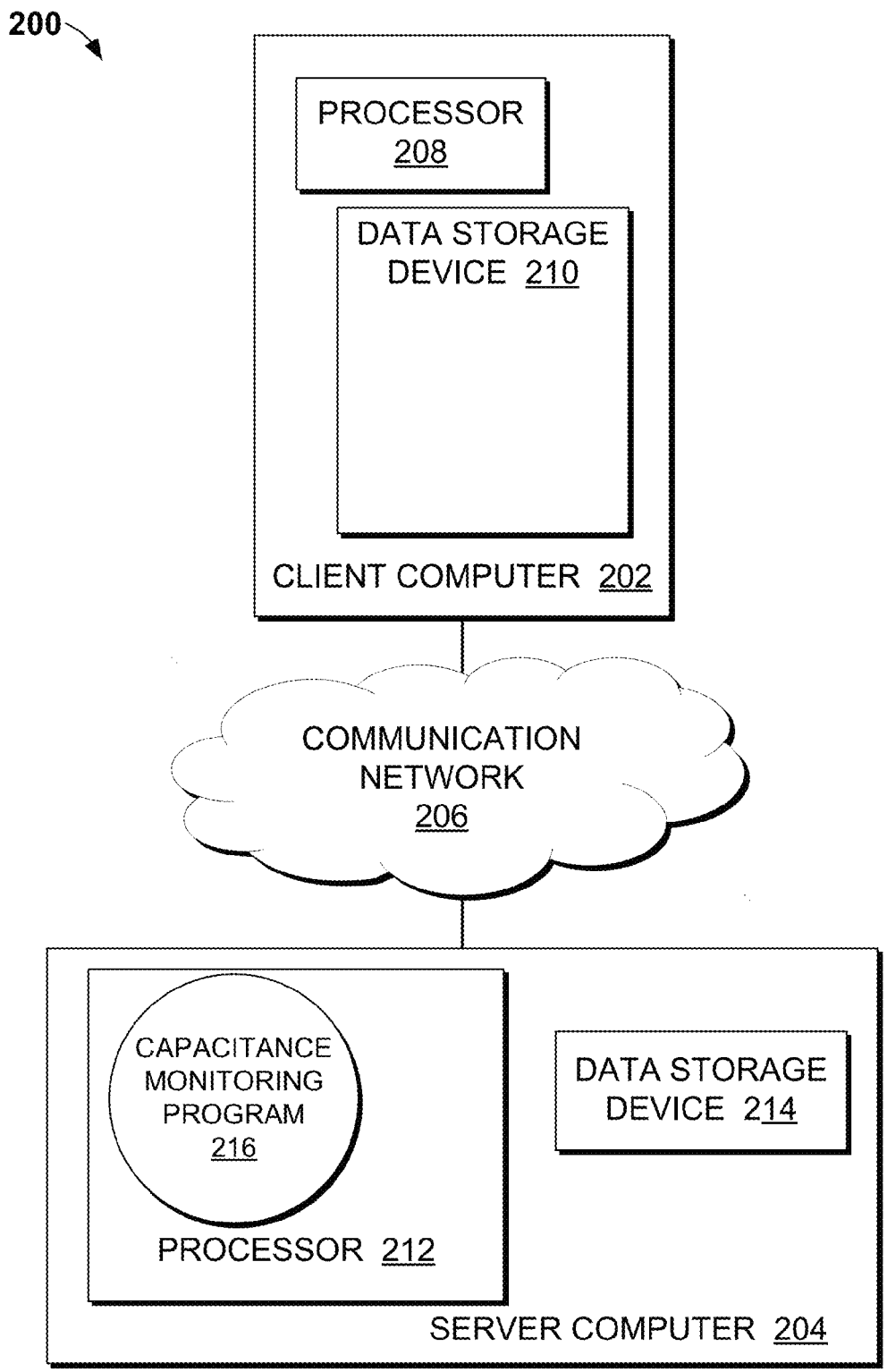
FIG. 6 illustrates a networked computer environment, according to an embodiment of the present disclosure.

Referring now to FIG. 6, a functional block diagram illustrating a system 200 for monitoring capacitance changes in deep trench (DT) capacitors using X-ray diffraction (XRD) measurements, in accordance with an embodiment of the present invention is shown. The system 200 may include a client computer 202 and a server computer 204. The client computer 202 may communicate with the server computer 204 via a communications network 206 (hereinafter "network"). The client computer 202 may include a processor 208 and a data storage device 210 that is enabled to interface with a user and communicate with the server computer 204. The server computer may also include a processor 212 and a data storage device 214 that is enabled to run a capacitance monitoring program 216. In an embodiment, the client computer 202 may operate as an input device including a user interface while the capacitance monitoring program 216 may run primarily on the server computer 204. It should be noted, however, that processing for the capacitance monitoring program 216 may, in some instances be shared amongst the client computer 202 and the server computer 204 in any ratio. In another embodiment, the capacitance monitoring program 216 may operate on more than one server computer 204, client computer 202, or some combination of server computers 204 and client computers 202, for example, a plurality of client computers 202 communicating across the network 206 with a single server computer 204.

The network 206 may include wired connections, wireless connections, fiber optic connections, or some combination thereof. In general, the network 206 can be any combination of connections and protocols that will support communications between the client computer 202 and the server computer 204. The network 206 may include various types of networks, such as, for example, a local area network (LAN), a wide area network (WAN) such as the Internet, a telecommunication network, a wireless network, a public switched network and/or a satellite network.

In various embodiments, the client computer 202 and/or the server computer 204 may be, for example, a laptop computer, tablet computer, netbook computer, personal computer (PC), a desktop computer, a personal digital assistant (PDA), a smart phone, a mobile device, or any programmable electronic device capable of communicating with the server computer 204 via the network 206. As described below with reference to FIG. 7, the client computer 202 and the server computer 204 may each include internal and external components.

In an embodiment, the system 200 may include any number of client computers 202 and/or server computers 204; however only one of each is shown for illustrative purposes only. It may be appreciated that FIG. 6 provides only an illustration of one implementation and does not imply any limitations with regard to the environments in which different embodiments may be implemented. Many modifications to the depicted environments may be made based on design and implementation requirements.

Figure 7:
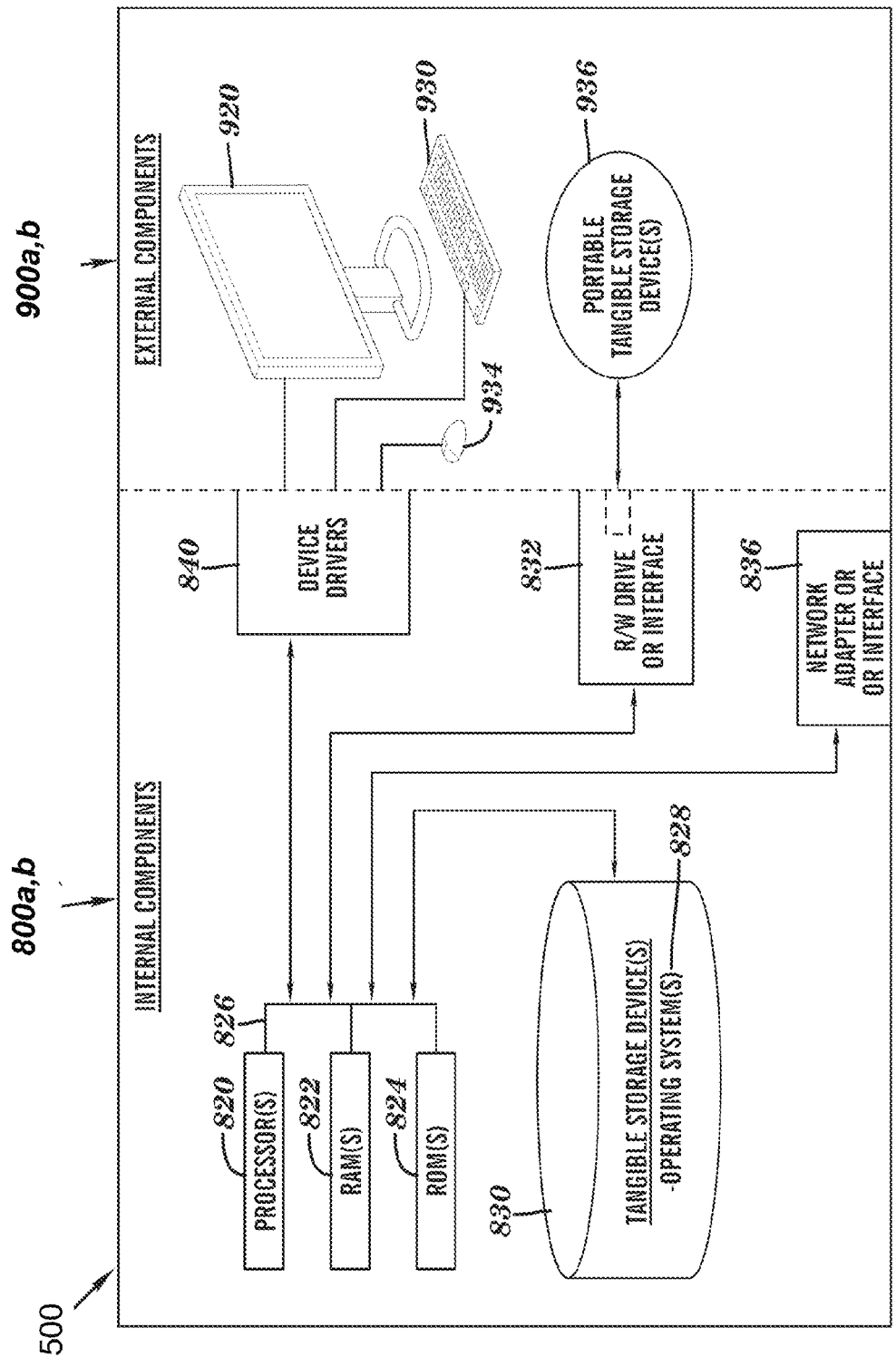
FIG. 7 is a block diagram of internal and external components of computers and servers depicted in FIG. 6 according to an embodiment of the present disclosure.

Referring now to FIG. 7, a block diagram 500 of internal and external components of the computers depicted in FIG. 6 is shown, according to an embodiment of the present disclosure. It should be appreciated that FIG. 6 provides only an illustration of one implementation and does not imply any limitations with regard to the environments in which different embodiments may be implemented. Many modifications to the depicted environments may be made based on design and implementation requirements.

Data processing system 800, 900 is representative of any electronic device capable of executing machine-readable program instructions. Data processing system 800, 900 may be representative of a smart phone, a computer system, PDA, or other electronic devices. Examples of computing systems, environments, and/or configurations that may be represented by data processing system 800, 900 include, but are not limited to, personal computer systems, server computer systems, thin clients, thick clients, hand-held or laptop devices, multiprocessor systems, microprocessor-based systems, network PCs, minicomputer systems, and distributed cloud computing environments that include any of the above systems or devices.

The client computer 202 and the server computer 204, both of FIG. 6, may include respective sets of internal components 800 *a, b* and external components 900 *a, b* illustrated in FIG. 7. Each of the sets of internal components 800 *a, b* includes one or more processors 820, one or more computer-readable RAMs 822 and one or more computer-readable ROMs 824 on one or more buses 826, and one or more operating systems 828 and one or more computer-readable tangible storage devices 830. The one or more operating systems 828 and programs, may be stored on one or more computer-readable tangible storage devices 830 for execution by one or more processors 820 via one or more RAMs 822 (which typically include cache memory). In the embodiment illustrated in FIG. 7, each of the computer-readable tangible storage devices 830 is a magnetic disk storage device of an internal hard drive. Alternatively, each of the computer-readable tangible storage devices 830 is a semiconductor storage device such as ROM 824, EPROM, flash memory or any other computer-readable tangible storage device that can store a computer program and digital information.

Each set of internal components 800 *a, b* also includes a R/W drive or interface 832 to read from and write to one or more portable computer-readable tangible storage devices 936 such as a CD-ROM, DVD, memory stick, magnetic tape, magnetic disk, optical disk or semiconductor storage device. The capacitance monitoring program 216 (FIG. 6) can be stored on one or more of the respective portable computer-readable tangible storage devices 936, read via the respective R/W drive or interface 832 and loaded into the respective hard drive 830.

Each set of internal components 800 *a, b* may also include network adapters (or switch port cards) or interfaces 836 such as a TCP/IP adapter cards, wireless Wi-Fi interface cards, or 3G or 4G wireless interface cards or other wired or wireless communication links. The capacitance monitoring program 216 (FIG. 6) in the server computer 204 (FIG. 6) can be downloaded from an external computer (e.g., server) via a network (for example, the Internet, a local area network or other, wide area network) and respective network adapters or interfaces 836. From the network adapters (or switch port adaptors) or interfaces 836, the capacitance monitoring program 216 (FIG. 6) in the server computer 204 (FIG. 6) may be loaded into the respective hard drive 830. The network may comprise copper wires, optical fibers, wireless transmission, routers, firewalls, switches, gateway computers and/or edge servers.

Each of the sets of external components 900 *a, b* can include a computer display monitor 920, a keyboard 930, and a computer mouse 934. External components 900 *a, b* can also include touch screens, virtual keyboards, touch pads, pointing devices, and other human interface devices. Each of the sets of internal components 800 *a, b* also includes device drivers 840 to interface to computer display monitor 920, keyboard 930 and computer mouse 934. The device drivers 840, R/W drive or interface 832 and network adapter or interface 836 comprise hardware and software (stored in storage device 830 and/or ROM 824).

Figure 8:
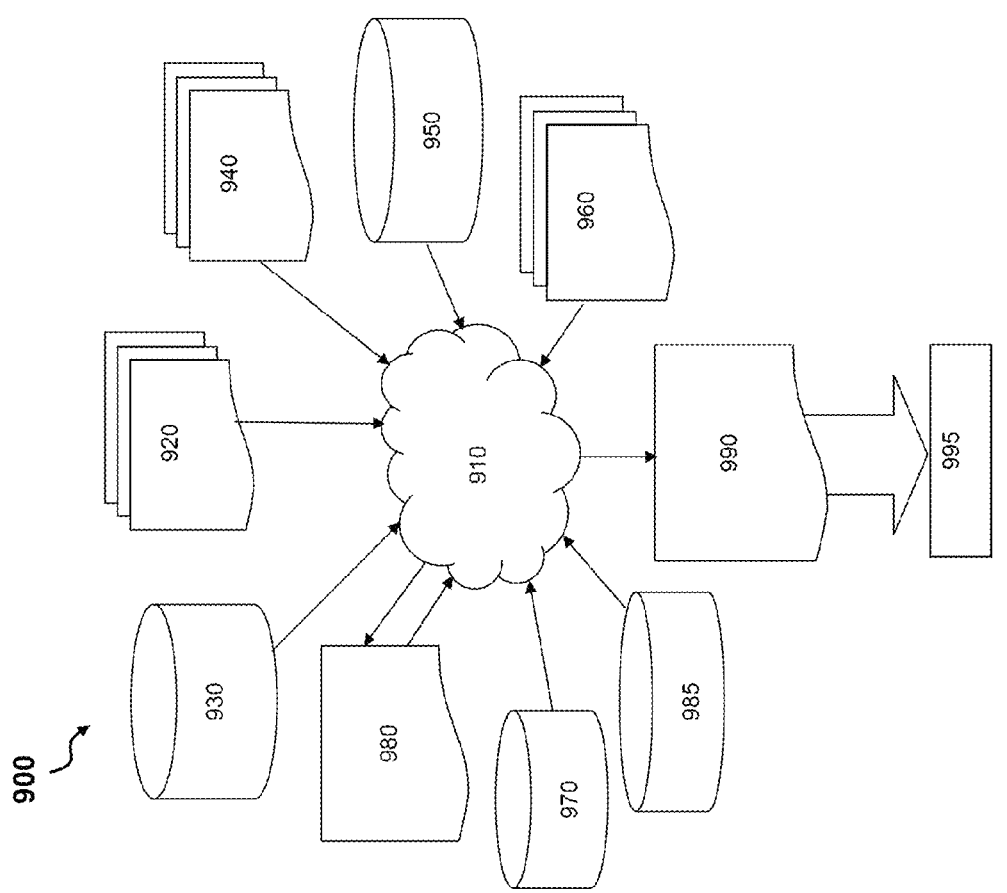
FIG. 8 is a flow diagram of a design process used in semiconductor design, manufacture, and/or test, according to an embodiment of the present disclosure.

Referring now to FIG. 8, a block diagram of an exemplary design flow 900 used, for example, in semiconductor IC logic design, simulation, test, layout, and manufacture, is shown. The design flow 900 includes processes, machines and/or mechanisms for processing design structures or devices to generate logically or otherwise functionally equivalent representations of the design structures and/or devices described above and shown in FIGS. 1-5. The design structures processed and/or generated by the design flow 900 may be encoded on machine readable transmission or storage media to include data and/or instructions that when executed or otherwise processed on a data processing system generate a logically, structurally, mechanically, or otherwise functionally equivalent representation of hardware components, circuits, devices, or systems. Machines include, but are not limited to, any machine used in an IC design process, such as designing, manufacturing, or simulating a circuit, component, device, or system. For example, machines may include: lithography machines, machines and/or equipment for generating masks (e.g. e beam writers), computers or equipment for simulating design structures, any apparatus used in the manufacturing or test process, or any machines for programming functionally equivalent representations of the design structures into any medium (e.g. a machine for programming a programmable gate array).

The design flow 900 may vary depending on the type of representation being designed. For example, a design flow 900 for building an application specific IC (ASIC) may differ from a design flow 900 for designing a standard component or from a design flow 900 for instantiating the design into a programmable array, for example a programmable gate array (PGA) or a field programmable gate array (FPGA) offered by Altera® Inc. or Xilinx® Inc.

FIG. 8 illustrates multiple such design structures including an input design structure 920 that is preferably processed by a design process 910. The design structure 920 may be a logical simulation design structure generated and processed by the design process 910 to produce a logically equivalent functional representation of a hardware device. The design structure 920 may also or alternatively comprise data and/or program instructions that when processed by the design process 910, generate a functional representation of the physical structure of a hardware device. Whether representing functional and/or structural design features, the design structure 920 may be generated using electronic computer-aided design (ECAD) such as implemented by a core developer/designer. When encoded on a machine-readable data transmission, gate array, or storage medium, the design structure 920 may be accessed and processed by one or more hardware and/or software modules within the design process 910 to simulate or otherwise functionally represent an electronic component, circuit, electronic or logic module, apparatus, device, or system such as those shown in FIGS. 1-5. As such, the design structure 920 may comprise files or other data structures including human and/or machine-readable source code, compiled structures, and computer-executable code structures that when processed by a design or simulation data processing system, functionally simulate or otherwise represent circuits or other levels of hardware logic design. Such data structures may include hardware-description language (HDL) design entities or other data structures conforming to and/or compatible with lower-level HDL design languages such as Verilog and VHDL, and/or higher level design languages such as C or C++.

The design process 910 preferably employs and incorporates hardware and/or software modules for synthesizing, translating, or otherwise processing a design/simulation functional equivalent of the components, circuits, devices, or logic structures shown in FIGS. 1-5 to generate a Netlist 980 which may contain design structures such as the design structure 920. The Netlist 980 may include, for example, compiled or otherwise processed data structures representing a list of wires, discrete components, logic gates, control circuits, I/O devices, models, etc. that describes the connections to other elements and circuits in an integrated circuit design. The Netlist 980 may be synthesized using an iterative process in which the Netlist 980 is resynthesized one or more times depending on design specifications and parameters for the device. As with other design structure types described herein, the Netlist 980 may be recorded on a machine-readable data storage medium or programmed into a programmable gate array. The medium may be a non-volatile storage medium such as a magnetic or optical disk drive, a programmable gate array, a compact flash, or other flash memory. Additionally, or in the alternative, the medium may be a system or cache memory, buffer space, or electrically or optically conductive devices and materials on which data packets may be transmitted and intermediately stored via the Internet, or other networking suitable means.

The design process 910 may include hardware and software modules for processing a variety of input data structure types including the Netlist 980. Such data structure types may reside, for example, within library elements 930 and include a set of commonly used elements, circuits, and devices, including models, layouts, and symbolic representations, for a given manufacturing technology (e.g., different technology nodes, 32 nm, 45 nm, 90 nm, etc.). The data structure types may further include design specifications 940, characterization data 950, verification data 960, design rules 970, and test data files 985 which may include input test patterns, output test results, and other testing information. The design process 910 may further include, for example, standard mechanical design processes such as stress analysis, thermal analysis, mechanical event simulation, process simulation for operations such as casting, molding, and die press forming, etc. One of ordinary skill in the art of mechanical design can appreciate the extent of possible mechanical design tools and applications used in the design process 910 without deviating from the scope and spirit of the invention. The design process 910 may also include modules for performing standard circuit design processes such as timing analysis, verification, design rule checking, place and route operations, etc.

The design process 910 employs and incorporates logic and physical design tools such as HDL compilers and simulation model build tools to process the design structure 920 together with some or all of the depicted supporting data structures along with any additional mechanical design or data (if applicable), to generate a second design structure 990. The second design structure 990 resides on a storage medium or programmable gate array in a data format used for the exchange of data of mechanical devices and structures (e.g. information stored in a IGES, DXF, Parasolid XT, JT, DRG, or any other suitable format for storing or rendering such mechanical design structures). Similar to the design structure 920, the second design structure 990 preferably comprises one or more files, data structures, or other computer-encoded data or instructions that reside on transmission or data storage media and that when processed by an ECAD system generate a logically or otherwise functionally equivalent form of one or more of the embodiments of the invention shown in FIGS. 1-5. In one embodiment, the second design structure 990 may comprise a compiled, executable HDL simulation model that functionally simulates the devices shown in FIGS. 1-5.

The second design structure 990 may also employ a data format used for the exchange of layout data of integrated circuits and/or symbolic data format (e.g. information stored in a GDSII (GDS2), GL1, OASIS, map files, or any other suitable format for storing such design data structures). The second design structure 990 may comprise information such as, for example, symbolic data, map files, test data files, design content files, manufacturing data, layout parameters, wires, levels of metal, vias, shapes, data for routing through the manufacturing line, and any other data required by a manufacturer or other designer/developer to produce a device or structure as described above and shown in FIGS. 1-5. The second design structure 990 may then proceed to a stage 995 where, for example, the second design structure 990: proceeds to tape-out, is released to manufacturing, is released to a mask house, is sent to another design house, is sent back to the customer, etc.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiment, the practical application or technical improvement over technologies found in the marketplace, or to enable others of ordinary skill in the art to understand the embodiments disclosed herein.

The invention claimed is:

1. A method comprising:
   measuring a difference between a primary X-ray diffraction peak and a secondary X-ray diffraction peak, the primary X-ray diffraction peak corresponds to an unstrained portion of a semiconductor substrate and the secondary X-ray diffraction peak corresponds to a strained portion of the semiconductor substrate,
   wherein the difference between the primary X-ray diffraction peak and the secondary X-ray diffraction peak comprises a delta shift peak that corresponds to changes in a crystal lattice caused by a stress applied to the strained portion of the semiconductor substrate,
   wherein the delta shift peak comprises variations in a deep trench capacitance.

2. The method of claim 1, wherein measuring the difference between the primary X-ray diffraction peak and the secondary X-ray diffraction peak comprises determining the delta shift peak after depositing a dielectric material in the deep trench.

3. The method of claim 1, further comprising:
   estimating dislocations in the crystal lattice of the semiconductor substrate caused during a high temperature annealing process based on the difference between the primary X-ray diffraction peak and the secondary X-ray diffraction peak.

4. A method comprising:
   forming a deep trench on a substrate;
   conducting a first X-ray diffraction measurement on the substrate, wherein a first X-ray diffraction peak is observed in the the first X-ray diffraction measurement;
   depositing a high-k dielectric material on the substrate and in the deep trench;
   conducting a second X-ray diffraction measurement on the substrate, wherein a second X-ray diffraction peak is observed in the second X-ray diffraction measurement;
   measuring a difference between a center of the first X-ray diffraction peak and a center of the second X-ray diffraction peak, wherein the difference between the center of the first X-ray diffraction peak and the center of the second X-ray diffraction peak comprises a delta peak shift;
   correlating, using a database, a plurality of previously measured delta peak shift and deep trench capacitance values to obtain a correlation curve, wherein a lower capacitance limit and an upper capacitance limit are set in the correlation curve based on the database; and comparing to the correlation curve the delta peak shift to determine a deep trench capacitance value, wherein continuing processing of the substrate depends on the deep trench capacitance value being above the lower capacitance limit and below the upper capacitance limit set in the correlation curve.

5. The method of claim 4, wherein the first X-ray diffraction measurement is conducted on an area of the substrate without the deep trench.

6. The method of claim 5, wherein the area of the substrate without the deep trench comprises an unstrained region of the substrate.

7. The method of claim 4, wherein the second X-ray diffraction measurement is conducted on an area of the substrate including the deep trench.

8. The method of claim 7, wherein the area of the substrate including the deep trench comprises a strained region of the substrate.

9. The method of claim 4, wherein measuring the difference between the center of the first X-ray diffraction peak and the center of the second X-ray diffraction peak comprises estimating changes in a crystal lattice of the substrate caused by a stress applied during deposition of the high-k dielectric material in the deep trench.

10. The method of claim 4, wherein the substrate comprises a silicon-containing semiconductor material.

11. The method of claim 4 further comprising:
conducting X-ray diffraction measurements before and after a high temperature annealing process on the substrate;
measuring the delta peak shift between X-ray diffraction measurements;
correlating, using a database, a plurality of previously measured delta peak shifts and known device leakage values to obtain a correlation curve, wherein an upper limit of device leakage is set in the correlation curve based on the database; and
comparing the delta peak shift to the correlation curve, wherein continuing processing of the substrate depends on a delta peak shift value corresponding to a device leakage value below the upper limit of device leakage.

12. The method of claim 11, wherein the high temperature annealing process causes dislocations in a crystal lattice of the substrate.

13. A computer program product comprising:
a computer readable non-transitory article of manufacture tangibly embodying computer readable instructions which, when executed, cause a computer to carry out a method comprising:
conducting a first X-ray diffraction measurement on a substrate before forming a deep trench in the substrate, wherein a first X-ray diffraction peak is observed in the first X-ray diffraction measurement;
conducting a second X-ray diffraction measurement on the substrate after depositing a high-k dielectric material in the deep trench, wherein a second X-ray diffraction peak is observed in the second X-ray diffraction measurement;
measuring a difference between a center of the first X-ray diffraction peak and a center of the second X-ray diffraction peak, wherein the difference between the center of the first X-ray diffraction peak and the center of the second X-ray diffraction peak comprises a delta peak shift;
correlating, using a database, a plurality of previously measured delta peak shift and deep trench capacitance values to obtain a correlation curve, wherein a lower capacitance limit and an upper capacitance limit are set in the correlation curve based on the database; and
comparing to the correlation curve the delta peak shift to determine a deep trench capacitance value, wherein continuing processing of the substrate depends on the deep trench capacitance value being above the lower capacitance limit and below the upper capacitance limit set in the correlation curve.

14. The computer program product of claim 13, wherein the first X-ray diffraction measurement is conducted on an area of the substrate without the deep trench.

15. The computer program product of claim 14, wherein the area of the substrate without the deep trench comprises an unstrained region of the substrate.

16. The computer program product of claim 13, wherein the second X-ray diffraction measurement is conducted on an area of the substrate including the deep trench.

17. The computer program product of claim 16, wherein the area of the substrate including the deep trench comprises a strained region of the substrate.

18. The computer program product of claim 13, wherein measuring the difference between the center of the first X-ray diffraction peak and the center of the second X-ray diffraction peak comprises estimating changes in a crystal lattice of the substrate caused by a stress applied during deposition of the high-k dielectric material.

19. The computer program product of claim 13 further comprising:
conducting X-ray diffraction measurements before and after a high temperature annealing process on the substrate;
measuring the delta peak shift between X-ray diffraction measurements;
correlating, using a database, a plurality of previously measured delta peak shifts and known device leakage values to obtain a correlation curve, wherein an upper limit of device leakage is set in the correlation curve based on the database; and
comparing the delta peak shift to the correlation curve, wherein continuing processing of the substrate depends on a delta peak shift value corresponding to a device leakage value below the upper limit of device leakage.

20. The computer program product of claim 19, wherein the high temperature annealing process causes dislocations in a crystal lattice of the substrate.

* * * * *